US00PP08117P

United States Patent [19]

van der Knapp

[11] Patent Number: Plant 8,117

[45] Date of Patent: Jan. 26, 1993

[54] CHRYSANTHEMUM PLANT—FUNSET CULTIVAR

[75] Inventor: Jacques C. M. van der Knapp, De Lier, Netherlands

[73] Assignee: Fides Beheer B.V., De Lier, Netherlands

[21] Appl. No.: 719,462

[22] Filed: Jun. 24, 1991

[51] Int. Cl.[5] ..... A01H 5/00

[52] U.S. Cl. ..... Plt./76

[58] Field of Search ..... Plt./74, 74.1, 82.4, Plt./82.5, 76, 80, 79, 81

*Primary Examiner*—Howard J. Locker

*Attorney, Agent, or Firm*—Burns, Doane, Swecker & Mathis

[57] ABSTRACT

A new and distinct cultivar of Chrysanthemum plant named Funset is provided. The new cultivar is a spontaneous mutation of the Funshine cultivar (U.S. Ser. No. 07/719,461, filed concurrently herewith) and can be readily distinguished from its parent cultivar. More specifically, the new cultivar forms attractive relatively small bicolored flowers wherein the petals are very light-red instead of white as the Funshine cultivar and the disc florets on the distal ends particularly towards the center bear an orange-red coloration (as illustrated) instead of the light-red coloration of the Funshine cultivar. The inflorescence tends to be pyramidal in configuration. The response period of the flowers is approximately seven and one-half weeks. The new cultivar is particularly suited for use in the production of a cut anemone spray under greenhouse conditions.

1 Drawing Sheet

SUMMARY OF THE INVENTION

The present invention comprises a new and distinct cultivar of Chrysanthemum, botanically known as *Chrysanthemum morifolium*, Ramat., and hereinafter is referred to by the cultivar name Funset.

The new Funset cultivar is a spontaneous mutation of unknown causation which was discovered and carefully preserved during the course of plant selection work which was conducted by me. The new cultivar was discovered during June, 1987 among plants of the Funshine cultivar (U.S. Ser. No. 07/719,461, filed concurrently herewith) being grown under my direct supervision at De Lier, The Netherlands.

It was observed that a plant consistently formed bicolored flowers with very light-red petals which included orange-red coloration on the distal ends of the disc florets (as illustrated) unlike the white petals and light-red disc coloration of the Funshine cultivar. All of the other characteristics of this plant were found to be substantially identical to those of the Funshine cultivar. Had I not discovered, carefully studied, and preserved this new cultivar, it would have been lost to manking. The new cultivar is particularly well suited for growing in the production of a cut anemone spray.

It was found that the new cultivar of the present invention:

(a) exhibits attractive relatively small anemone flowers having an overall diameter of approximately 40 mm. wherein the petals are very light-red and the disc florets particularly towards the center bear an orange-red coloration on the distal ends, (b) bears flowers in a somewhat pyramidal configuration, (c) exhibits a flower response period of approximately seven and one-half weeks, (d) forms attractive dark green foliage, and (e) has the ability to produce flowers of commercially acceptable quality throughout the year in a cut mum production program.

Asexual reproduction of the new cultivar by cuttings as performed at De Lier, The Netherlands, in a controlled environment has demonstrated that the characteristics of the new cultivar as herein disclosed are firmly fixed and are retained through successive generations of asexual propagation.

Funset has not been observed under all possible environmental conditions to date. Accordingly, it is possible that the phenotype may vary somewhat with variations in the environment, such as temperature, light, day length, contact with pesticides and/or subjection to growth retardant treatments.

When the new cultivar of the present invention is compared to the Improved Funshine cultivar (U.S. Ser. No. 07/719,464, filed concurrently herewith), it is noted that the Improved Funshine cultivar exhibits white petals and a stronger and more intense red coloration on the distal ends of the disc florets than the parent Funshine cultivar. When the new cultivar of the present invention is compared to the Funbeam cultivar (U.S. Ser. No. 07/719,463, filed concurrently herewith), it is noted that the Funbeam cultivar exhibits light red-purple petals, and more intense coloration on the distal ends of the disc florets than the Funshine and Improved Funshine cultivars. When the new cultivar of the present invention is compared to the Funrise cultivar (U.S. Ser. No. 07/719,465, filed concurrently herewith), it is noted that the Funrise cultivar exhibits red-purple petals which tend to be slightly darker than those of the Funbeam cultivar and tends to exhibit a less intense red coloration on the distal ends of the disc florets than the Improved Funshine cultivar. When the new cultivar of the present invention is compared to the Funglow cultivar (U.S. Ser. No. 07/720,211, filed concurrently herewith), it is noted that the Funglow cultivar exhibits yellow petals and greyed-purple coloration on the distal ends of the disc florets.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at De Lier, The Netherlands.

DETAILED DESCRIPTION

The chart used in the identification of colors described hereafter is the R.H.S. Colour Chart of The Royal Horticultural Society, London, England. The color values were determined at 11:00 a.m. to 12:00 noon under natural daylight conditions at De Lier, The Netherlands, during May, 1991. The plants described were grown under standard greenhouse conditions which approximate those commonly utilized for the production of cut mums.

Classification:

*Botanical.*—*Chrysanthemum morifolium* Ramat., cv. Funset.

*Commercial.*—Cut anemone spray.

Inflorescence

A. Capitulum:

*Form.*—Pyramidal.

*Type.*—Anemone.

*Diameter across face.*—Approximately 40 mm. on average.

*Diameter of flower center.*—Approximately 25 mm. on average.

B. Corolla of ray and disc florets:

*Color(General tonality from a distance of three meters).*—Very light-red with orange-red center.

*Color ray florets (top surface).*—Very light-red, Red Group 36D.

*Color disc florets.*—Orange-red, Orange-Red Group 34B.

C. Reproductive organs:

*Androecium.*—Not present.

*Gynoecium.*—Present in both ray and disc florets.

Plant

A. General appearance:

*Height.*—Approximately 90 cm. on average.

B. Foliage:

*Color (upper surface).*—Yellow-Green Group 147A.

*Color (under surface).*—Yellow-Green Group 147B.

I claim:

1. A new and distinct cultivar of Chrysanthemum plant named Funset, substantially as herein shown and described, which:

(a) exhibits attractive relatively small anemone flowers having an overall diameter of approximately 40 mm. wherein the petals are very light-red and the disc florets particularly towards the center bear an orange-red coloration on the distal ends, (b) bears flowers in a somewhat pyramidal configuration, (c) exhibits a flower response period of approximately seven and one-half weeks, (d) forms attractive dark green foliage, and (e) has the ability to produce flowers of commercially acceptable quality throughout the year in a cut mum production program.

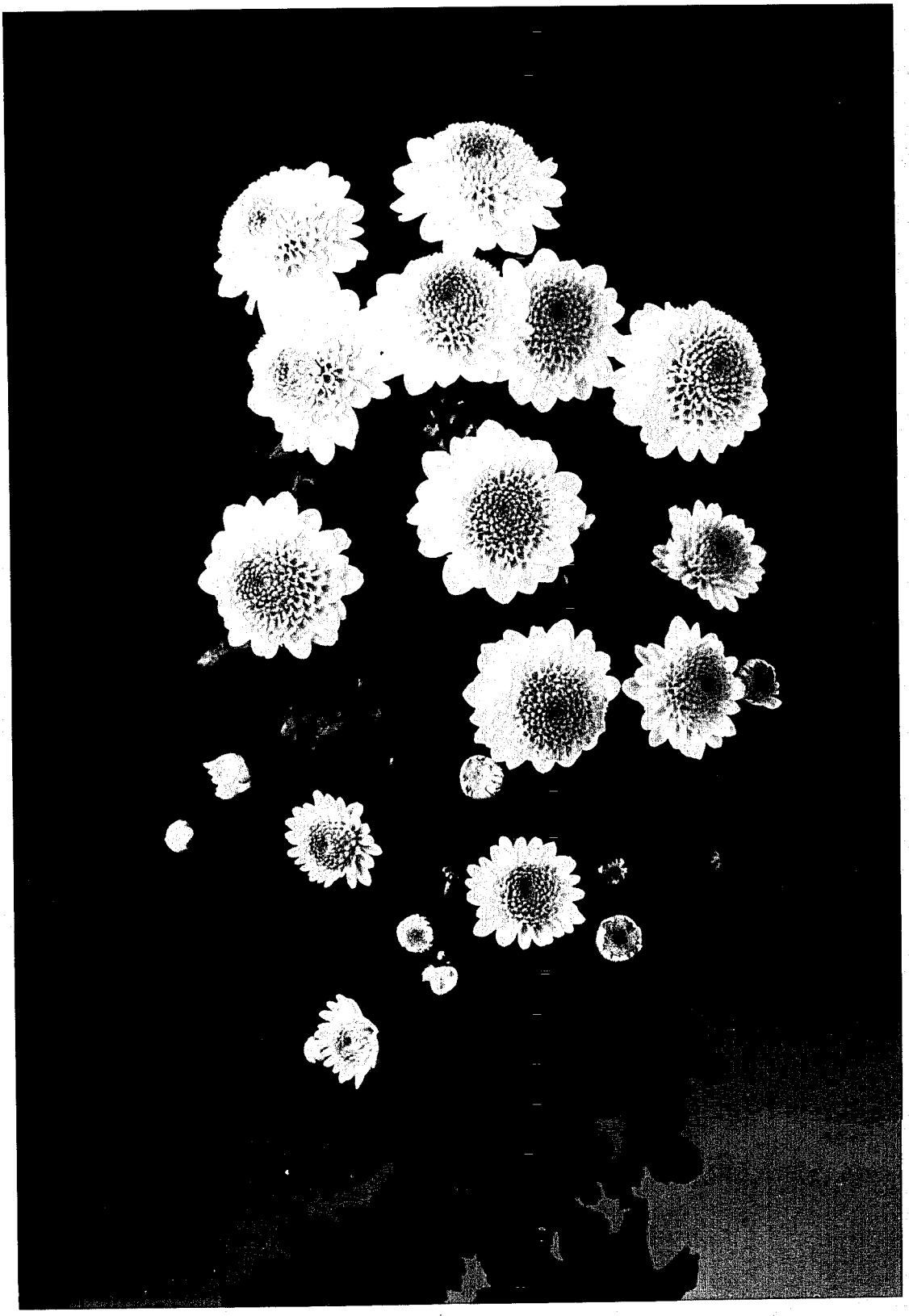

* * * * *